US009445989B2

United States Patent
Harrison et al.

(10) Patent No.: US 9,445,989 B2
(45) Date of Patent: Sep. 20, 2016

(54) TOPICAL WOUND TREATMENT METHOD AND COMPOSITION

(71) Applicant: Wake Forest University Health Sciences, Winston-Salem, NC (US)

(72) Inventors: Benjamin S. Harrison, Tobaccoville, NC (US); Steve J. Hodges, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/382,175

(22) PCT Filed: Mar. 1, 2013

(86) PCT No.: PCT/US2013/028615
§ 371 (c)(1),
(2) Date: Aug. 29, 2014

(87) PCT Pub. No.: WO2013/130969
PCT Pub. Date: Sep. 6, 2013

(65) Prior Publication Data
US 2015/0024053 A1    Jan. 22, 2015

Related U.S. Application Data

(60) Provisional application No. 61/605,813, filed on Mar. 2, 2012.

(51) Int. Cl.
*A61K 9/00* (2006.01)
*A61K 9/14* (2006.01)
(Continued)

(52) U.S. Cl.
CPC ............ *A61K 9/0014* (2013.01); *A61J 1/05* (2013.01); *A61K 9/06* (2013.01); *A61K 9/14* (2013.01);
(Continued)

(58) Field of Classification Search
CPC .......... A61K 31/327; A61K 2300/00; A61K 31/17; A61K 45/06; A61K 47/02; A61K 47/10; A61K 47/12; A61K 47/14; A61K 47/44; A61K 9/0014; A61K 9/06; A61K 9/14; A61J 1/05
See application file for complete search history.

(56) References Cited

U.S. PATENT DOCUMENTS

| 4,623,536 A * | 11/1986 | Winston et al. ................ 424/49 |
| 2003/0224054 A1 | 12/2003 | Gibbins et al. |
| 2009/0252815 A1 | 10/2009 | Walzer et al. |

FOREIGN PATENT DOCUMENTS

| JP | 60-261600 | * 12/1985 | ............ A01K 63/04 |
| WO | WO 2004/091675 A1 | * 10/2004 | ............ A61L 15/24 |

(Continued)

OTHER PUBLICATIONS

International Search Report and Written Opinion, PCT/US13/28615, mailed May 14, 2013.

*Primary Examiner* — Aradhana Sasan
(74) *Attorney, Agent, or Firm* — Myers Bigel & Sibley, P.A.

(57) ABSTRACT

A topical wound treatment composition comprises a hydrogen peroxide generator; alkaline powder; not more than 5 percent by weight of water; additional topical active agent if desired, and emollient (preferably hygroscopic emollient) to balance. When topically applied to a wound and water from the surrounding environment diffuses into the composition, the hydrogen peroxide generator and/or the alkaline compound diffuse into one another, causing a chemical reaction that generates treatment-effective amounts of oxygen to occur. The oxygen can then diffuse out of the composition and aid in wound treatment or healing.

18 Claims, 2 Drawing Sheets

Oxygen Generation

(51) Int. Cl.
 *A61K 31/17* (2006.01)
 *A61K 47/12* (2006.01)
 *A61K 47/10* (2006.01)
 *A61K 47/44* (2006.01)
 *A61K 9/06* (2006.01)
 *A61K 47/14* (2006.01)
 *A61K 47/02* (2006.01)
 *A61K 45/06* (2006.01)
 *A61K 31/327* (2006.01)
 *A61J 1/05* (2006.01)

(52) U.S. Cl.
 CPC ............. *A61K 31/17* (2013.01); *A61K 31/327* (2013.01); *A61K 45/06* (2013.01); *A61K 47/02* (2013.01); *A61K 47/10* (2013.01); *A61K 47/12* (2013.01); *A61K 47/14* (2013.01); *A61K 47/44* (2013.01)

(56) References Cited

FOREIGN PATENT DOCUMENTS

WO    WO 2006/029351 A2    3/2006
WO    WO 2012/140535 A1    10/2012

* cited by examiner

FIGURE 1: Untreated
FIGURE 2: Treated

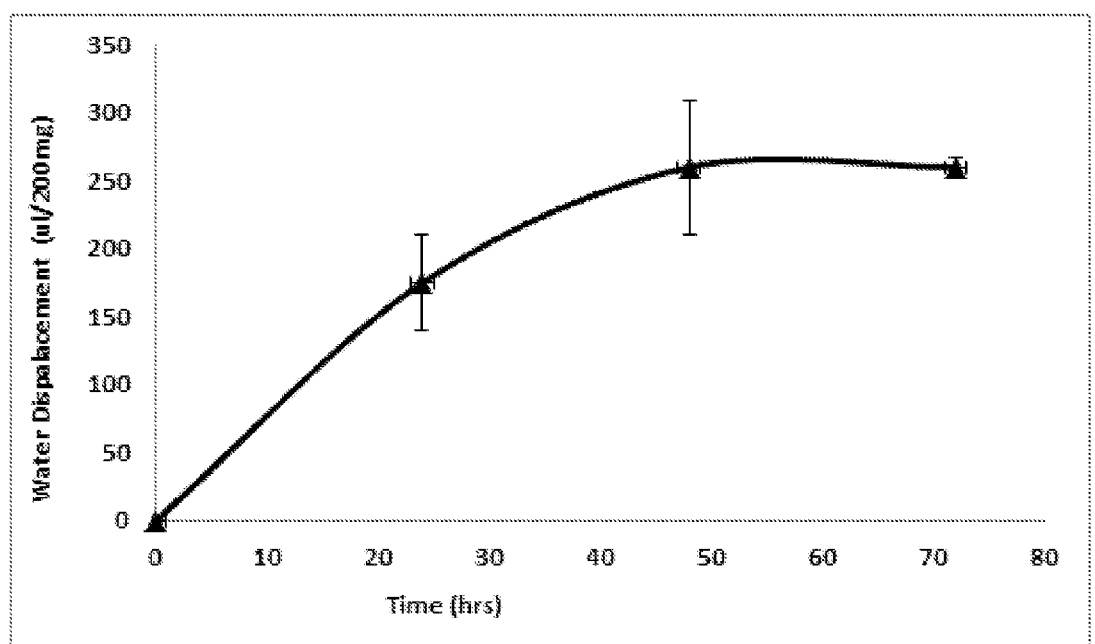
FIGURE 3: Oxygen Generation

TOPICAL WOUND TREATMENT METHOD AND COMPOSITION

RELATED APPLICATIONS

This application is a 35 U.S.C. §371 national phase entry of PCT Application PCT/US2013/028615, filed Mar. 1, 2013, and published in English on Sep. 6, 2013, as International Publication No. WO 2013/130969, and which claims the benefit of U.S. Provisional Application No. 61/605,813, filed Mar. 2, 2012, the disclosure of each of which is incorporated herein by reference in its entirety.

FIELD OF THE INVENTION

The present invention concerns methods and compositions for the treatment of wounds such as incisions, particularly for promoting or enhancing the healing thereof.

BACKGROUND OF THE INVENTION

Wound healing is a complex regeneration process, which is characterized by degradation and re-assembly of connective tissue and epidermal layer. The pH value within the wound-milieu influences (directly and indirectly) all biochemical reactions taking place in this process of healing. Interestingly, it is so far a neglected parameter for the overall outcome.

For more than three decades the common assumption amongst physicians was that a low pH value, such as it is found on normal skin, is favorable for wound healing. However, investigations have shown that some healing processes, such as the take-rate of skin-grafts, actually require an alkaline milieu. The matter is thus much more complicated than was previously assumed.

One review suggests that wound pH is a potent influential factor for the healing process and that different pH ranges are required for certain distinct phases of wound healing (L. Schneider et al., Influence of pH on wound-healing: a new perspective for wound-therapy? *Arch Dermatol. Res.* 298: 413-420 (2007)). Further systematic data needs to be collected for a better understanding of the pH requirements under specific circumstances. This may be important as it may help to develop new pH targeted therapeutic strategies.

Another common agent used in wound treatments is hydrogen peroxide. It has been hypothesized that hydrogen peroxide would accelerate reepithelization and/or have a positive effect on infection. Unfortunately, the results of using hydrogen peroxide alone do not appear to support this hypothesis.

One report using a combination of baking soda and hydrogen peroxide on post-surgical wound healing showed a significant increase in wound healing from oral surgery (A. Dentino et al., Effect of a baking soda-peroxide dentifrice on post-surgical wound healing, *American Journal of Dentistry* 8(3): 125-7 (1995)). In this report the effects of twice daily brushing with a baking soda-hydrogen peroxide dentifrice or a placebo dentifrice were observed over a 28-day post-surgical period. At days 7 and 14, soft tissue appearance/wound healing (STA) was assessed based on color and edema. Post-surgical wound healing was statistically significantly improved at day 7 with the trend continuing to day 14 when sodium bicarbonate-hydrogen peroxide was used as compared to a control. Such materials were shown to be a possibly effective aid in the early phase of healing following gingival flap surgery. However, the compositions used were designed for oral surgery, and were not adapted to other forms of treatment. Accordingly, there is a need for new compositions and methods for treating wounds.

SUMMARY OF THE INVENTION

The present invention is based on the finding that a topical wound treatment composition can be provided by dispersing a solid particulate hydrogen peroxide generator (e.g. urea peroxide) into an emollient (e.g. an ointment or moisturizer) to form a composition, and dispersing particles of an alkaline powder into the composition. When topically applied to a wound and water from the surrounding environment diffuses into the composition, the hydrogen peroxide generator and/or the alkaline compound diffuse into one another, causing a chemical reaction that generates treatment-effective amounts of oxygen to occur. The oxygen can then diffuse out of the composition and aid in wound treatment or healing.

A first aspect of the invention is a topical wound treatment composition comprising, consisting of, or consisting essentially of:

(a) from 0.05, 0.1 or 0.2 to 15, 20 or 30 percent by weight of a hydrogen peroxide generator;

(b) from 0.05 or 0.1 to 20 or 30 percent by weight of alkaline powder;

(c) not more than 1, 2, 3, 4, or 5 or percent by weight of water;

(d) optionally, from 0 or 0.01 to 10 or 20 percent by weight of an additional topical active agent; and (e) emollient to balance.

The composition optionally but preferably has a pH less than 7 or 8. (e.g., a pH of from 4 to 6, 7 or 8).

In some embodiments, the hydrogen peroxide generator is a solid particulate (e.g., a solid particulate that consists essentially of particles having a diameter of from 10, 50 or 100 nanometers up to 1, 10, or 25 microns) that is dispersed in the emollient.

In some embodiments, the alkaline powder is a solid particulate (e.g., a solid particulate that consists essentially of particles having a diameter of from 10, 50 or 100 nanometers up to 1, 10, or 25 microns) that is dispersed in the emollient.

In some embodiments, the hydrogen peroxide generator and said alkaline powder are included in a molar ratio of between 4:1 or 2:1 and 1:2 or 1:4.

A further aspect of the invention is a method of treating a wound in a subject in need thereof, comprising: topically applying to the wound a composition as described herein in a treatment-effective amount.

In some embodiments, the pH of the composition, and/or the emollient in the composition decreases to less than 7 or 6 within three, six, 12, or 24 hours of said topical application.

A further aspect of the invention is the use of a composition as described herein for carrying out a method as described herein.

The present invention is explained in greater detail in the drawings herein and the specification set forth below. The disclosures of all US Patent references cited herein are to be incorporated by reference herein in their entirety.

BRIEF DESCRIPTION OF THE DRAWINGS

FIG. 1 is a photograph of the first of two inguinal surgical incisions in a bilateral patient 28 days after closure, which incision was otherwise left untreated.

FIG. 2 is a photograph of the second of two inguinal surgical incisions in the same patient as FIG. 1, again 28 days after closure, which incision was treated with an oxygen-generating gel of the present invention. Note the pronounced enhancement in healing in FIG. 2 as compared to FIG. 1.

FIG. 3 shows oxygen generation from a composition of the present invention.

DETAILED DESCRIPTION OF THE PREFERRED EMBODIMENTS

The present invention is primarily concerned with the treatment of human subjects, but the invention may also be carried out on animal subjects, particularly mammalian subjects such as dogs, cats, livestock and horses for veterinary purposes. While subjects may be of any suitable age, the subjects are in some embodiments neonatal, infant, juvenile, adolescent, adult, or geriatric subjects.

"Treat" as used herein refers to any type of treatment that imparts a benefit to an aging patient, particularly delaying or retarding the progression of aging.

"Pharmaceutically acceptable" as used herein means that the compound or composition is suitable for administration to a subject to achieve the treatments described herein, without unduly deleterious side effects in light of the severity of the disease and necessity of the treatment.

A. Compositions.

The compositions of the invention generally comprise, consist of or consist essentially of a hydrogen peroxide generator, an alkaline powder, and an emollient, and optionally an additional active ingredient, each of which is discussed further below. Additional conventional (generally pharmaceutically acceptable) ingredients such as preservatives, stabilizers, buffers, colorants, or the like can optionally be included in minor amounts if desired, in accordance with known techniques.

Hydrogen Peroxide Generator (HPG).

Any suitable hydrogen peroxide generator can be used. Examples include, but are not limited to, urea peroxide, sodium percarbonate, hydrogen peroxide, sodium perborate, potassium percarbonate, potassium perborate, calcium peroxide, magnesium peroxide, metal peroxide, or mixtures thereof. Urea peroxide is currently preferred.*

The amount of the hydrogen peroxide generator in the composition can be from 0.1 or 0.5 to 15 or 20 percent by weight. Higher concentrations can be used so long as the amount of hydrogen peroxide generated does not exceed 3% by weight, as this is the limit generally regarded as safe for use in humans.

In one embodiment, the composition includes 3 percent by weight of urea peroxide, which generates approximately one percent by weight of hydrogen peroxide.

When the hydrogen peroxide generator is a powder that does not readily dissolve in the emollient, the average diameters of the particles within the hydrogen peroxide generator are in general, 10, 50 or 100 nanometers up to 1, 10, or 25 microns. In some embodiments, particles of from 100 nanometers to 1 micron in diameter are preferred. Particle size, along with other aspects of the composition, can be selected to control the rate of oxygen generation.

Urea peroxide will need a small amount of acid present to keep the pH at approximately 5. DEBROX brand urea peroxide compositions uses citric acid to impart the acidic pH. Other acids that may be used include, but are not limited to, citric acid, ascorbic acid, benzoic acid, succinic acid, glycolic acid, lactic acid, and anhydrides thereof. In general, the concentration of the acid or anhydride is approximately 0.01 to 1 percent by weight.

Akaline Powder (AP).

The alkaline powder creates an environment where the pH makes hydrogen peroxide unstable, resulting in hydrogen peroxide decomposition into oxygen. As hydrogen peroxide becomes increasingly susceptible to decomposition above pH 5, the alkaline powder compound should be in sufficient concentration to create an alkaline environment. It is preferred that the resulting pH be between pH 5 or 6 and and pH 9 and more preferred between pH 7 and 8.5.

The alkaline powder or compound can be any number of powdered bases available. Suitable materials may include the alkali and alkaline earth metal salts of carbonate, bicarbonate, citrate, phosphate, and acetate. Preferred bases are sodium carbonate, sodium bicarbonate, potassium carbonate, potassium bicarbonate, sodium acetate, potassium acetate, sodium citrate, potassium citrate, sodium phosphate, potassium phosphate, etc. In some embodiments, sodium carbonate and sodium bicarbonate are preferred.

The average diameters of the alkaline powder particles is preferably between 10 or 100 nanometers up to 1, 10, or 25 microns. In some embodiments, a particle size between 100 nanometers to 1 micron is preferred. As with other properties, particle size allows control over the rate of oxygen generation, with smaller particles allowing more rapid generation of an alkaline environment and increase decomposition rate of hydrogen peroxide.

The amount of the alkaline powder can, in general, be between 0.1 or 0.5 to 15 or 20 percent by weight in the composition but preferably at a molar ratio of between 2:1 and 1:2, or more preferably a molar ratio of 1:1, hydrogen peroxide generator to alkaline powder.

Emollients.

The emollient is, in general, a viscous binder in which the hydrogen peroxide generator and alkaline powder are dissolved or suspended. It is viscous in nature to slow down the diffusion of HPG and AP to prevent premature reaction before application. The emollient also helps to draw moisture into the ointment to cause the reaction to proceed. In addition it makes the application of the hydrogen peroxide generator and the alkaline powder to the wound site easier as it will keep the components from moving from the site of application once it is applied. It is important that the amount of water in the emollient should be minimized to hinder a premature reaction between the HPG and AP. Water should be less than 2 or 1 percent by weight. The emollient makes up the balance of the composition. In some embodiments, it is composed of ingredients found in humectant moisturizers which typically contain as its main ingredient a polyol such as as glycerol, propylene glycol, caprylil glycerol, polymeric polyols (like polydextrose), glyceryl triacetate, lactic acid or glycolic acid.

In general, any suitable emollient compound or combination thereof can be used to carry out the present invention. Examples of classes of emollients and examples thereof include, but are not limited to, those set forth in Reller et al., U.S. Pat. No. 4,199,576 (Procter & Gamble), as follows:

1. Hydrocarbon oils and waxes. Examples thereof are mineral oil, petrolatum, parrafin, ceresin, ozokerite, microcrystalline wax, polyethylene, and perhydrosqualene.
2. Silicone oils, such as dimethyl polysiloxanes, methylphenyl polysiloxanes, water-soluble and alcohol-soluble silicone glycol copolymers.

3. Triglyceride esters, for example vegetable and animal fats and oils. Examples include castor oil, safflower oil, cottonseed oil, corn oil, olive oil, cod liver oil, almond oil, avocado oil, palm oil, sesame oil, and soybean oil.
4. Acetoglyceride esters, such as acetylated monoglycerides.
5. Ethoxylated glycerides, such as ethoxylated glyceryl monostearate.
6. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
7. Alkenyl esters of fatty acids having 10 to 20 carbon atoms. Examples thereof include oleyl myristate, oleyl stearate, and oleyl oleate.
8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.
9. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanol alcohols are examples of satisfactory fatty alcohols.
10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups.
11. Ether-esters such as fatty acid esters of ethoxylated fatty alcohols.
12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.
13. Polyhydric alcohols and polyether derivatives. Propylene glycol, dipropylene glycol, polypropylene glycol 2000, 4000, polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol 200-6000, methoxy polyethylene glycols 350, 550, 750, 2000, 5000, poly[ethylene oxide] homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$-$C_{18}$ vicinal glycol, and polyoxypropylene derivatives of trimethylolpropane are examples thereof.
14. Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
15. Wax esters such as beeswax, spermaceti, myristyl myristate, stearyl stearate.
16. Beeswax derivatives, e.g. polyoxyethylene sorbitol beeswax. These are reaction products of beeswax with ethoxylated sorbitol of varying ethylene oxide content, forming a mixture of ether-esters.
17. Vegetable waxes including carnauba and candelilla waxes.
18. Phospholipids such as lecithin and derivatives.
19. Sterols. Cholesterol, cholesterol fatty acid esters are examples thereof.
20 Amides such as fatty acid amides, ethoxylated fatty acid amides, solid fatty acid alkanolamides.

See also U.S. Pat. Nos. 5,051,449; 5,122,519; 5,446,063; 5,492,894; 6,440,465; 6,887,490; 7,731,993; and 7,976,854.

The compositions of the present invention can also further comprise or consist essentially of from 1% or 2 percent by weight to 5 or 10 percent by weight of an emulsifier. Emulsifiers are of a nonionic, anionic or cationic class. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglyceride wherein the fatty acid moiety contains from 10 to 20 carbon atoms, diethylene glycol, polyethylene glycols of molecular weight 200 to 6000, propylene glycol of molecular weight 200 to 3000, glycerol, sorbitol, sorbitan, polyoxyethylene sorbitol, polyoxyethylene sorbitan, and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceeding paragraphs also have emulsifying properties. When a lotion is formulated containing such an emollient, an additional emulsifier is not needed, though it can be included in the composition. See, e.g., U.S. Pat. No. 4,199,576.

In some embodiments, the emollient or composition is hygroscopic (that is, takes up and retains water from the surrounding environment, such as atmospheric water vapor, and/or liquid water from a tissue or tissue surface). The particular degree of hygroscopicity is not critical and will vary from formulation to formulation depending upon factors such as the particular intended use. In some embodiments, the emollient, and/or the composition, absorbs at least about 0.1, 0.5, 1, 5 or 10 percent by weight water (up to 50 or 80 percent by weight water, or more) within a 24 hour period in a humidity chamber maintained at 60 percent relative humidity and 25 degrees Centigrade at atmospheric pressure.

Additional Active Agents.

On or more additional active ingredient can optionally be included in any suitable amount, typically (when included) in an amount of from 0.01 to 5 or 10 percent by weight. Examples of such other active ingredients include, but are not limited to, retinols such as retin-A, hydroquinone, antibiotics, topical analgesics, etc., including combinations thereof. Additional examples include but are not limited to those topical active agents described in U.S. Pat. Nos. 7,758,888; 7,645,803; 7,404,967; 6455,076; and 5,804,203, the disclosures of which are incorporated by reference herein in their entirety.

Water, Packaging and Application.

In general, the compositions comprise less than 5, 4, 3, 2 or 1 percent by weight water, and more preferably less than 1 percent by weight, of water so that the pH of the composition is generally not greater than 6 or 7 (e.g., between 4 or 5, up to 6 or 7) prior to application. As noted above, the emollient can be selected to be one that is hygroscopic, or has humectant properties, so that water is drawn in to the composition (from skin and/or the atmosphere) after application, the pH of the composition is raised above 6 or 7, and the oxygen-generating reactions go forward. Humectant emollients such as LUBRIDERM® brand intense skin repair ointment are suitable.

The composition can be packaged in a suitable container that is water impermeable/substantially excludes atmospheric moisture, such as a syringe, foil tube, or the like, for subsequent use, in accordance with known techniques. In the alternative, the ingredients can be kept separate and provided in a "kit" form for mixing into the final composition just prior to use. For example, the hydrogen peroxide generator can be provided in a first container, optionally mixed with emollient, and the alkaline powder in a second container, optionally mixed with emollient. In general, at least one or the other is preferably mixed with an emollient; in some embodiments, both are mixed with an emollient (the same emollient, or a subset of ingredients of the final emollient composition). One or the other, or both, can be mixed with an additional active agent as described above. The two separate mixtures can be packaged separately (e.g., in a vial, syringe, tube or the like), and the two packages combined in a further package or container as a kit for subsequent use.

B. Subjects and Methods of Use.

As noted above, the compositions of the present invention are suitable for use in both human subjects and in animal subjects (particularly mammalian subjects such as dogs, cats, horses, pigs, cattle, etc.) for veterinary purposes. The subject may be male or female and of any suitable age, including neonate, infant, juvenile, adolescent, adult, and geriatric subjects.

The compositions may be topically applied to any of a variety of wounds. Examples include, but are not limited to, incisions (including surgical incisions), lacerations, abrasions (such as in dermabrasion and microdermabrasions), ulcers, burns (including first, second, and third degree burns, and "chemical peel" or laser resurfacing burns), etc.

In some embodiments, the wound is a degloving injury to an animal limb, such as a degloving injury of a horse's leg.

In some embodiments, the wound is a diabetic wound ulcer.

The wound may the result of an accidental injury or be the consequence of a medical procedure. The wound may be a surgical incision. The wound may be an ischemic tissue flap, such as in the course of cosmetic surgery. The wound may be be one caused in the course of other cosmetic surgery, such as dermabrasion, microdermabrasion, chemical peel, laser resurfacing, etc.

The wound may be a chronic injury, such as photodamage, aged skin, wrinkles, bags under they eyes, etc.

An oxygen-impermeable dressing (e.g., an adhesive polymeric film) may be applied to the subject over the composition, after the composition is applied to the wound, to reduce the amount of generated oxygen escaping to the atmosphere, and increase the amount of generated oxygen available to the wound.

The present invention is explained in greater detail in the following non-limiting Examples.

EXAMPLE 1

Preparation of Oxygen-Producing Gel

Note: All procedures in this Example are to be carried out in a clean, sterile environment. Aseptic techniques are used.

Preparation of Syringe #1: A 5-mL sterile syringe is acquired; the plunger is removed and set aside. The plunger barrel is charged with Lubriderm Intense Skin Repair Ointment, UPC 5280048201, (4 ml) and the plunger is carefully replaced into the syringe. The syringe is placed in an upright position, and the plunger is slowly depressed to expel excess air and reduce the volume of LUBRIDERM® brand Intense Skin Repair Ointment in the syringe to 3.0 mL.

Preparation of Syringe #2: A 5-mL sterile syringe equipped with a needle is charged with DEBROX® brand 6.5% carbamide peroxide dispersed in glycerin (3.0 ml).

A 10 to 25 mL container is tared on a balance (that is accurate to at least 0.01 grams) and charged with USP grade sodium bicarbonate powder (1.0 g). The beaker is charged with the contents of syringe #1 and the contents of syringe #2. The components are thoroughly mixed with a stirring rod for one minute to generate the POG-UPO-Gel. A 5-mL sterile syringe is acquired; the plunger is removed and set aside. The plunger barrel is charged with POG-UPO-Gel (1.5 mL) and the plunger is carefully replaced into the syringe. The syringe is placed in an upright position and the plunger is slowly depressed to expel excess air and reduce the volume of POG-UPO-Gel in the syringe to 1.0 mL. The syringe is capped and placed into a 50 mL conical tube. Additional 5-mL sterile syringes may be charged, capped and stored as described above. The syringes charged with POG-UPO-Gel are labeled: POG-UPO-Gel; Single Use Only; Contents: 1 mL mixture of POG-UPO-Gel; Directions: Apply to wound; cover with an oxygen impermeable dressing; Storage: 0-25° C. in a dry, cool place.

Note: The charged syringes can be stored in a refrigerator or at room temperature in a cool, dry place. Contact with moisture will rapidly degrade the product.

EXAMPLE 2

The Effect of an Oxygen Producing Gel on Wound Healing of Bilateral Similar Inguinal Incisions A subject with bilateral similar inguinal incisions (i.e. bilateral orchidopexy, bilateral hernia repair) was treated as follows: The first side incision was dressed using a standard surgical dressing. The incision remained covered for 48 hours following discharge and was photographed 2 weeks post surgery (see FIG. 1). The second side incision was treated with POG-UPO-Gel (1 ml) and covered with an oxygen impermeable dressing that remained in place for 48 fours following discharge. The POG-UPO-Gel treated incision was photographed 2 weeks post surgery (see FIG. 2).

EXAMPLE 3

Oxygen Generation

Oxygen generation from the formulation described in Examples 1-2 above was measured using a water displacement method. Briefly, 200 mg of the material was spread onto the plunger of a 60 ml syringe followed by the addition of 6 ml water. The needle was inserted into an inverted 1 ml graduate pipette filled with water. As oxygen was generated within the syringe, the gas traveled to the pipette and displaced the water within the pipette. The displacement of water was recorded and used to calculate the amount of oxygen generated. Oxygen generation was measured over time showing that oxygen was generated up to 48 hours after application.

The foregoing is illustrative of the present invention, and is not to be construed as limiting thereof. The invention is defined by the following claims, with equivalents of the claims to be included therein.

That which is claimed is:

1. A topical wound treatment composition, comprising:
   (a) from 0.1 to 20 percent by weight of a solid particulate hydrogen peroxide generator;
   (b) from 0.1 to 20 percent by weight of alkaline powder, wherein said alkaline powder is in the form of a solid particulate that consists essentially of particles having a diameter of from 10 nanometers up to 25 microns;
   (c) not more than 2 percent by weight of water;
   (d) from 0 to 10 percent by weight of an additional topical active agent; and
   (e) emollient to balance;
   said composition having a pH less than 7.

2. The composition of claim 1, wherein said hydrogen peroxide generator is selected from the group consisting of urea peroxide, sodium percarbonate, hydrogen peroxide, sodium perborate, potassium percarbonate, potassium perborate, calcium peroxide, magnesium peroxide, and mixtures thereof.

3. The composition of claim 1, wherein said hydrogen peroxide generator is urea peroxide.

4. The composition of claim 1, wherein said solid particulate consists essentially of particles having a diameter of from 10 nanometers up to 25 microns.

5. The composition of claim 1, wherein said alkaline powder is selected from the group consisting of sodium carbonate, sodium bicarbonate, potassium carbonate, potassium bicarbonate, sodium acetate, potassium acetate, sodium citrate, potassium citrate, sodium phosphate, and potassium phosphate.

6. The composition of claim 5, wherein said alkaline powder is selected from the group consisting of sodium carbonate and sodium bicarbonate.

7. The composition of claim 1, wherein said emollient has a pH of from 4 to 6.

8. The composition of claim 1, wherein said composition comprises not more than 1 percent by weight of water.

9. The composition of claim 1, wherein said hydrogen peroxide generator and said alkaline powder are included in a molar ratio of between 2:1 and 1:2.

10. The composition of claim 1, wherein said additional active agent is selected from the group consisting of retinols, hydroquinone, antibiotics, topical analgesics, and combinations thereof.

11. The composition of claim 1, wherein said emollient is hygroscopic.

12. The composition of claim 1 sealed in a water impermeable container.

13. A method of treating a wound in a subject in need thereof, comprising:
   (a) topically applying to said wound a composition in a treatment-effective amount, said composition comprising:
      (i) from 0.1 to 20 percent by weight of a solid particulate hydrogen peroxide generator;
      (ii) from 0.1 to 20 percent by weight of alkaline powder, wherein said alkaline powder is in the form of a solid particulate that consists essentially of particles having a diameter of from 10 nanometers up to 25 microns;
      (iii) not more than 2 percent by weight of water;
      (iv) from 0 to 10 percent by weight of an additional topical active agent; and
      (v) emollient to balance;
   said composition having a pH less than 7; and
   (b) applying an oxygen-impermeable dressing to said subject over said composition.

14. The method of claim 13, wherein said pH of said emollient in said composition decreases to less than 6 within six hours of said topical application.

15. The method of claim 13, wherein said wound is selected from the group consisting of incisions, abrasions, lacerations, burns, and ulcerations.

16. The method of claim 13, wherein said hydrogen peroxide generator and/or said alkaline compound diffuse into one another after said applying step upon uptake of water and generate oxygen in a treatment-effective amount.

17. The composition of claim 1, wherein:
   said hydrogen peroxide generator is urea peroxide;
   said alkaline powder is selected from the group consisting of sodium carbonate and sodium bicarbonate; and
   said hydrogen peroxide generator and said alkaline powder are included in a molar ratio of between 2:1 and 1:2.

18. The method of claim 13, wherein:
   said hydrogen peroxide generator is urea peroxide;
   said alkaline powder is selected from the group consisting of sodium carbonate and sodium bicarbonate; and
   said hydrogen peroxide generator and said alkaline powder are included in a molar ratio of between 2:1 and 1:2.

* * * * *